US012582797B2

(12) United States Patent
Hanbury

(10) Patent No.: US 12,582,797 B2
(45) Date of Patent: Mar. 24, 2026

(54) METHODS AND SYSTEMS FOR TREATING ANXIETY AND DEPRESSION

(71) Applicant: SANA HEALTH, INC., Lafayette, CO (US)

(72) Inventor: Richard Hanbury, Lafayette, CO (US)

(73) Assignee: SANA HEALTH, INC., Lafayette, CO (US)

( * ) Notice: Subject to any disclaimer, the term of this patent is extended or adjusted under 35 U.S.C. 154(b) by 1237 days.

(21) Appl. No.: 17/319,759

(22) Filed: May 13, 2021

(65) Prior Publication Data

US 2021/0353904 A1    Nov. 18, 2021

Related U.S. Application Data

(60) Provisional application No. 63/026,192, filed on May 18, 2020.

(51) Int. Cl.
*A61M 21/02* (2006.01)
*A61M 21/00* (2006.01)

(52) U.S. Cl.
CPC ..... *A61M 21/02* (2013.01); *A61M 2021/0027* (2013.01); *A61M 2021/0044* (2013.01); *A61M 2210/0612* (2013.01); *A61M 2210/0662* (2013.01); *A61M 2230/06* (2013.01); *A61M 2230/08* (2013.01); *A61M 2230/10* (2013.01); *A61M 2230/50* (2013.01); *A61M 2230/63* (2013.01); *A61M 2230/65* (2013.01)

(58) Field of Classification Search
CPC .......... A61M 21/02; A61M 2021/0027; A61M 2021/0044; A61M 2210/0612; A61M 2210/0662; A61M 2230/06; A61M 2230/08; A61M 2230/10; A61M 2230/50; A61M 2230/63; A61M 2230/65; A61M 2205/332; A61M 2230/60
USPC ...................................................... 600/26–28
See application file for complete search history.

(56) References Cited

U.S. PATENT DOCUMENTS

| 4,172,406 A | 10/1979 | Martinez |
| 4,315,502 A | 2/1982 | Gorges |
| 4,892,106 A | 1/1990 | Gleeson, III |
| 4,966,164 A | 10/1990 | Colsen et al. |
| 5,343,261 A | 8/1994 | Wilson |

(Continued)

FOREIGN PATENT DOCUMENTS

| CN | 205814527 U | 12/2016 |
| CN | 104546285 B | 3/2017 |

(Continued)

OTHER PUBLICATIONS

Kubios HRV (ver. 3.1) User's Guide, by Tarvainen et al. Feb. 27, 2018 (see attached) (Year: 2018).*

(Continued)

*Primary Examiner* — Sunita Reddy
(74) *Attorney, Agent, or Firm* — Dickinson Wright PLLC; Kristopher Lance Anderson; Alexander Courtade

(57) ABSTRACT

Non-pharmaceutical methods of treating the symptoms of anxiety and depression are described. The method includes providing a person with stimuli include visual and/or auditory stimuli which are pulsed at the rate of various types of brain waves. The use of the method greatly lessens various symptoms of anxiety and depression, including one or more of pain, anxiety, depression, and problems sleeping.

12 Claims, 8 Drawing Sheets

700

| Repeat the following Segments C1-C4 6 times for a total of 12 minutes | Auditory Left | Auditory Right | Light Left | Light Right |
|---|---|---|---|---|
| Segment C1 (light and auditory both sides pulse together) | On 1 sec | On 1 sec | On 1 sec | On 1 sec |
| Repeat 15 times, followed by 1 sec gap | Off 1 sec | Off 1 sec | Off 1 sec | Off 1 sec |
| Segment C2 (light and auditory on left side, alternating light and auditory on right) | On 1 sec | Off 1 sec | On 1 sec | Off 1 sec |
| Repeat 15 times, followed by 1 sec gap | Off 1 sec | On 1 sec | Off 1 sec | On 1 sec |
| Segment C3 (both lights together, alternating with both auditory signals together) | On 1 sec | On 1 sec | Off 1 sec | Off 1 sec |
| Repeat 14 times, followed by 1 sec gap | Off 1 sec | Off 1 sec | On 1 sec | On 1 sec |
| Segment C4 (auditory left and light right together, alternating auditory right and light left together) | On 1 sec | Off 1 sec | Off 1 sec | On 1 sec |
| Repeat 144 times, followed by 1 sec gap | Off 1 sec | On 1 sec | On 1 sec | Off 1 sec |

(56) References Cited

U.S. PATENT DOCUMENTS

| | | | |
|---|---|---|---|
| 5,783,909 | A | 7/1998 | Hochstein |
| 6,123,661 | A | 9/2000 | Fukushima et al. |
| 6,409,655 | B1 | 6/2002 | Wilson et al. |
| 8,562,659 | B2 | 10/2013 | Wells et al. |
| 8,838,247 | B2 | 9/2014 | Hagedorn et al. |
| 8,852,073 | B2 | 10/2014 | Genereaux et al. |
| 8,932,199 | B2 | 1/2015 | Berka et al. |
| D775,260 | S | 12/2016 | Gordon et al. |
| 9,649,469 | B2 | 5/2017 | Hyde et al. |
| D805,515 | S | 12/2017 | Bowes et al. |
| D827,701 | S | 9/2018 | Nguyen et al. |
| 10,328,236 | B2 | 6/2019 | Hanbury |
| 10,383,769 | B1 | 8/2019 | Miller |
| 10,449,326 | B2 | 10/2019 | Genereux et al. |
| 2002/0198577 | A1 | 12/2002 | Jaillet |
| 2006/0106276 | A1 | 5/2006 | Shealy et al. |
| 2006/0252979 | A1 | 11/2006 | Vesely et al. |
| 2008/0269629 | A1 | 10/2008 | Reiner |
| 2009/0156886 | A1 | 6/2009 | Burgio et al. |
| 2010/0056854 | A1 | 3/2010 | Chang |
| 2010/0161010 | A1 | 6/2010 | Thomas |
| 2010/0323335 | A1 | 12/2010 | Lee |
| 2011/0075853 | A1 | 3/2011 | Anderson |
| 2011/0213664 | A1 | 9/2011 | Osterhout et al. |
| 2011/0257712 | A1 | 10/2011 | Wells et al. |
| 2012/0095534 | A1 | 4/2012 | Schlangen et al. |
| 2012/0211013 | A1 | 8/2012 | Otis |
| 2013/0035734 | A1 | 2/2013 | Soler et al. |
| 2013/0225915 | A1 | 8/2013 | Redfield et al. |
| 2013/0267759 | A1 | 10/2013 | Jin |
| 2013/0303837 | A1 | 11/2013 | Berka et al. |
| 2014/0336473 | A1 | 11/2014 | Greco |
| 2015/0231395 | A1 | 8/2015 | Saab |
| 2015/0268673 | A1 | 9/2015 | Farzbod et al. |
| 2016/0228771 | A1 | 8/2016 | Watson |
| 2017/0143935 | A1 | 5/2017 | Hanbury |
| 2017/0189639 | A1 | 7/2017 | Mastrianni |
| 2017/0252532 | A1 | 9/2017 | Holsti et al. |
| 2017/0312476 | A1 | 11/2017 | Woo |
| 2018/0184969 | A1 | 7/2018 | Zhao et al. |
| 2018/0250494 | A1 | 9/2018 | Hanbury |
| 2019/0030279 | A1 | 1/2019 | Nowlin |
| 2019/0192077 | A1 | 6/2019 | Kaiser et al. |
| 2019/0262576 | A1 | 8/2019 | Mastrianni |
| 2019/0388020 | A1 | 12/2019 | Stauch et al. |
| 2020/0139112 | A1 | 5/2020 | Aharonovitch |
| 2020/0268341 | A1 | 8/2020 | Stroman |
| 2020/0324139 | A1* | 10/2020 | Wingren ............... A61N 5/0618 |
| 2020/0368491 | A1 | 11/2020 | Poltorak |
| 2021/0008332 | A1 | 1/2021 | Jin et al. |

FOREIGN PATENT DOCUMENTS

| | | | |
|---|---|---|---|
| WO | 2001064005 | A2 | 9/2001 |
| WO | 2012117343 | A1 | 9/2012 |
| WO | 2015028480 | A1 | 3/2015 |
| WO | 2016140408 | A1 | 9/2016 |
| WO | 2019060598 | A1 | 3/2019 |
| WO | 2020219350 | A1 | 10/2020 |

OTHER PUBLICATIONS

European Patent Office, Extended European Search Report dated Nov. 27, 2020 for European Patent Application No. 18761087.8, 9 pages.

Intellectual Property India, Examination Report for Application No. 201837022885, dated May 6, 2021; 7 pages.

International Searching Authority, Search Report and Written Opinion in PCT/US2020/41423, mailed Oct. 9, 2020; 9 pages.

International Searching Authority, Search Report and Written Opinion in PCT/US2020/019091, mailed May 6, 2020; 13 pages.

Chinnakkaruppan Adaikkan, et al., "Gamma Entrainment Binds Higher-Order Brain Regions and Offers Neuroprotection", Neuron, https://linkinghub.elsevier.com/retrieve/pii/S0896627319303460, May 7, 2019 (May 7, 2019), 18 Pages.

Liviu Aron, et al., "Neural synchronization in Alzheimer's disease", Nature, Journal, vol. 540, Dec. 7, 2016 (Dec. 7, 2016), pp. 207-208.

Pam Belluck, "Could simply listening to this sound help cure Alzheimer's disease? MIT researchers are Investigating", Boston Globe, https://www.bostonglobe.com/news/science/2019/03/14/could-simply-listening-this-sound-help-cure-alzheimer-disease-mit-researchers-are-investigating/2npZrAp8g9KLSfURbTxaVO/story.html, Mar. 14, 2019 (Mar. 14, 2019), 4 Pages.

Pam Belluck, "A Possible Alzheimer's Treatment With Clicks and Flashes? It Worked on Mice", New York Times, https://www.nytimes.com/2019/03/14/health/alzheimers-memory.html, Mar. 14, 2019 (Mar. 14, 2019), 5 Pages.

Angus Chen, "An Hour of Light and Sound a Day Might Keep Alzheimer's at Bay", Scientific American, https://www.scientificamerican.com/article/an-hour-of-light-and-sound-a-day-might-keep-alzheimers-at-bay/, Mar. 14, 2019 (Mar. 14, 2019), 5 Pages.

Aimee Corso, "Cognito Therapeutics Launched with Exclusive License to Promising Alzheimer's Research from The Massachusetts Institute of Technology", Business Wire, Boston and San Francisco, https://www.businesswire.com/news/home/20161207006042/en/Cognito-Therapeutics-Launched-Exclusive-License-Promising-Alzheimer%E2%80%99s, Dec. 7, 2016 (Dec. 7, 2016), 3 Pages.

Hannah Devlin, "Strobe lighting provides a flicker of hope in the fight against Alzheimer's", The Guardian, https://www.theguardian.com/science/2016/dec/07/strobe-lighting-provides-a-flicker-of-hope-in-the-fight-against-alzheimers, Dec. 7, 2016 (Dec. 7, 2016), 3 Pages.

Jamie Ducharme, "The End of Alzheimer's?", Boston, Magazine, https://www.bostonmagazine.com/health/2017/11/27/li-huei-tsai-alzheimers-treatment/, Nov. 27, 2017 (Nov. 27, 2017), 4 Pages.

Damian Garde, "'Beyond amyloid': A look at what's next in Alzheimer's research", STAT, https://www.statnews.com/2017/08/18/beyond-amyloid-alzheimers-research/, Aug. 18, 2017 (Aug. 18, 2017), 5 Pages.

Melissa Healy, "Flickering lights may illuminate a path to Alzheimer's treatment", Los Angeles Times, Dec. 7, 2016 (Dec. 7, 2016), 3 Pages.

Nathan Hurst, "Could Flickering Lights Help Treat Alzheimer's?", Smithsonian, https://www.smithsonianmag.com/innovation/could-flickering-lights-help-treat-alzheimers-180961762/, Jan. 11, 2017 (Jan. 11, 2017), 2 Pages.

Hannah F. Iaccarino, et al., "Gamma frequency entrainment attenuates amyloid load and modifies microglia", Nature, Journal, vol. 540, Dec. 7, 2016 (Dec. 7, 2016), pp. 230-235.

Anthony J. Martorell, et al., "Multi-sensory Gamma Stimulation Ameliorates Alzheimer's-Associated Pathology and Improves Cognition", Cell, https://www.cell.com/cell/fulltext/S0092-8674(19)30163-1, Mar. 14, 2019 (Mar. 14, 2019), 16 Pages.

Helen Thomson, "How flashing lights and pink noise might banish Alzheimer's, improve memory and more", Nature, https://www.nature.com/articles/d41586-018-02391-6, Feb. 28, 2018 (Feb. 28, 2018), 10 Pages.

Meg Tirrell, "Could flashing light treat Alzheimer's? Fresh approaches to treating the disease", CNBC, https://www.cnbc.com/2017/03/29/could-flashing-light-treat-alzheimers-fresh-approaches-to-treating-the-disease.html, Mar. 29, 2017 (Mar. 29, 2017), 6 Pages.

Anne Trafton, "Ed Boyden receives 2018 Canada Gardner International Award", McGovern Institute, https://mcgovern.mit.edu/2018/03/27/ed-boyden-receives-2018-canada-gairdner-international-award/, Mar. 27, 2018 (Mar. 27, 2018), 3 Pages.

Molly Webster, et al., "Bringing Gamma Back", WNYC Studios, https://www.wnycstudios.org/story/bringing-gamma-back, Dec. 8, 2016 (Dec. 8, 2016), 3 Pages.

Robert Weisman, "MIT team uses LEDs to attack Alzheimer's ", Boston Globe, https://www.bostonglobe.com/business/2016/12/07/led-technology-from-mit-used-startup-working-alzheimer-treatment/Kbdjp9WvfoPLfC1bNhvGOI/story.html, Dec. 7, 2016 (Dec. 7, 2016), 4 Pages.

(56) References Cited

OTHER PUBLICATIONS

Nicole Wetsman, "Flickering light seems to help mice with Alzheimer's-like symptoms", Popular Science, https://www.popsci.com/flickering-light-genes-alzheimers, May 7, 2019 (May 7, 2019), 2 Pages.

Ed Yong, "Beating Alzheimer's With Brain Waves", The Atlantic, https://www.theatlantic.com/science/archive/2016/12/beating-alzheimers-with-brain-waves/509846/, Dec. 7, 2016 (Dec. 7, 2016), 8 Pages.

NSTC, "First Friday Biosciences: Nov. 3 in Woburn", https://www.nstc.org/previous-events/first-friday-biosciences-nov-3-in-woburn/, Nov. 3, 2017 (Nov. 3, 2017), 8 Pages.

The Picower Institute, "Tsai earns Hans Wigzell Research Foundation Science Prize", https://picower.mit.edu/news/tsai-earns-hans-wigzell-research-foundation-science-prize, Jan. 23, 2019 (Jan. 23, 2019), 3 Pages.

PCT Search Report, mailed May 7, 2018 in International Application PCT/US2018020547, filed Mar. 1, 2018, 2 pages.

PCT Search Report, mailed Feb. 3, 2017 in International Application PCT/US2016063651, filed Nov. 23, 2016, 4 pages.

European Patent Office, Supplementary European Search Report mailed Jun. 5, 2019 for European Patent Application No. 16869299.4, 8 pages.

The International Searching Authority, Notification of Transmittal of the International Search Report and the Written Opinion of the International Searching Authority mailed Aug. 2, 2019 in International Application No. PCT/US19/033322, 11 pages.

Illumy by Sound Oasis; https://www.soundoasis.com/products/light-therapy/illumy-the-smart-sleep-mask/; Product description downloaded Aug. 2, 2021; 6 pages Copyright 2000-2021 AvivaHealth.com.

Remee Lucid Dreaming Mask; http://sleepwithremee.com/; Product description downloaded Aug. 3, 2021; 10 pages; Copyright 2018 Bitbanger LLC.

Lumos Smart Sleep Mask; https://lumos.tech/lumos-smart-sleep-mask/; Product description downloaded Aug. 3, 2021; 3 pages.

Dreamlight Zen; https://dreamlight.tech/products/dreamlight-zen; product description downloaded Aug. 3, 2021; 16 pages; Copyright 2021 Dreamlight.

International Search Report and Written Opinion in PCT/US2021/032260, mailed Aug. 31, 2021; 9 pages.

Szafir, et al., Pay Attention Designing Adaptive Agents that Monitor and Improve User Engagement, Conference on Human Factors in Computing Systems, May 5, 2012, 10 Pages.

Patent Cooperation Treaty, International Preliminary Report on Patentability for PCT/US2021/032260, mailed Dec. 1, 2022; 8 pages.

* cited by examiner

| Segments A1-A4 for 120s | Auditory Left | Auditory Right | Light Left | Light Right |
|---|---|---|---|---|
| Segment A1 (light and auditory both sides pulse together) | On 0.1277 sec | On 0.1277 sec | On 0.1277 sec | On 0.1277 sec |
| Repeat 116 times, followed by 0.5 sec gap | Off 0.1277 sec | Off 0.1277 sec | Off 0.1277 sec | Off 0.1277 sec |
| Segment A2 (light and auditory on left side, alternating light and auditory on right) | On 0.1277 sec | Off 0.1277 sec | On 0.1277 sec | Off 0.1277 sec |
| Repeat 116 times, followed by 0.5 sec gap | Off 0.1277 sec | On 0.1277 sec | Off 0.1277 sec | On 0.1277 sec |
| Segment A3 (both lights together, alternating with both auditory signals together) | On 0.1277 sec | On 0.1277 sec | Off 0.1277 sec | Off 0.1277 sec |
| Repeat 115 times, followed by 0.5 sec gap | Off 0.1277 sec | Off 0.1277 sec | On 0.1277 sec | On 0.1277 sec |
| Segment A4 (auditory left and light right together, alternating auditory right and light left together) | On 0.1277 sec | Off 0.1277 sec | Off 0.1277 sec | On 0.1277 sec |
| Repeat 115 times, followed by 0.5 sec gap | Off 0.1277 sec | On 0.1277 sec | On 0.1277 sec | Off 0.1277 sec |

FIG. 5

| Segments B1-B4 for 120s | Auditory Left | Auditory Right | Light Left | Light Right |
|---|---|---|---|---|
| Segment B1 (light and auditory both sides pulse together) Repeat 45 times, followed by 0.5 sec gap | On 0.3333 sec | On 0.3333 sec | On 0.3333 sec | On 0.3333 sec |
| | Off 0.3333 sec | Off 0.3333 sec | Off 0.3333 sec | Off 0.3333 sec |
| Segment B2 (light and auditory on left side, alternating light and auditory on right) Repeat 45 times, followed by 0.5 sec gap | On 0.3333 sec | Off 0.3333 sec | On 0.3333 sec | Off 0.3333 sec |
| | Off 0.3333 sec | On 0.3333 sec | Off 0.3333 sec | On 0.3333 sec |
| Segment B3 (both lights together, alternating with both auditory signals together) Repeat 44 times, followed by 0.5 sec gap | On 0.3333 sec | On 0.3333 sec | Off 0.3333 sec | Off 0.3333 sec |
| | Off 0.3333 sec | Off 0.3333 sec | On 0.3333 sec | On 0.3333 sec |
| Segment B4 (auditory left and light right together, alternating auditory right and light left together) Repeat 44 times, followed by 0.5 sec gap | On 0.3333 sec | Off 0.3333 sec | Off 0.3333 sec | On 0.3333 sec |
| | Off 0.3333 sec | On 0.3333 sec | On 0.3333 sec | Off 0.3333 sec |

FIG. 6

| Repeat the following Segments C1-C4 6 times for a total of 12 minutes | Auditory Left | Auditory Right | Light Left | Light Right |
|---|---|---|---|---|
| Segment C1 (light and auditory both sides pulse together) Repeat 15 times, followed by 1 sec gap | On 1 sec | On 1 sec | On 1 sec | On 1 sec |
| | Off 1 sec | Off 1 sec | Off 1 sec | Off 1 sec |
| Segment C2 (light and auditory on left side, alternating light and auditory on right) Repeat 15 times, followed by 1 sec gap | On 1 sec | Off 1 sec | On 1 sec | Off 1 sec |
| | Off 1 sec | On 1 sec | Off 1 sec | On 1 sec |
| Segment C3 (both lights together, alternating with both auditory signals together) Repeat 14 times, followed by 1 sec gap | On 1 sec | On 1 sec | Off 1 sec | Off 1 sec |
| | Off 1 sec | Off 1 sec | On 1 sec | On 1 sec |
| Segment C4 (auditory left and light right together, alternating auditory right and light left together) Repeat144 times, followed by 1 sec gap | On 1 sec | Off 1 sec | Off 1 sec | On 1 sec |
| | Off 1 sec | On 1 sec | On 1 sec | Off 1 sec |

FIG. 7

Sleep Quality PSQI at Baseline and End of Study

FIG. 8

METHODS AND SYSTEMS FOR TREATING ANXIETY AND DEPRESSION

CROSS-REFERENCE TO RELATED APPLICATIONS

This application claims priority to U.S. Provisional Patent Application Ser. No. 63/026,192, filed on May 18, 2020, the entire disclosure of which is incorporated herein by reference.

BACKGROUND

The present disclosure generally relates to treating people suffering from anxiety and depression, and more particularly to a method and system of treating the symptoms of anxiety and depression.

Anxiety and depression are mental health disorders characterized by feelings of worry, anxiety, or fear that are strong enough to interfere with a person's daily activities. Many people suffer from both anxiety and depression. Examples of anxiety disorders include panic attacks, post-traumatic stress disorder, and obsessive-compulsive disorder. Symptoms of the anxiety disorders include high levels of stress that are often out of proportion to an event impacting the stress, the inability to set aside a worry, and restlessness.

People with depression often experience symptoms similar to those of an anxiety disorder. Symptoms of depression include an overwhelming feeling of sadness, a loss of interest, a pleasure in most usual activities, nervousness, irritability, and issues with concentrating and sleeping. Other symptoms include a decrease or increase in appetite, psycho motor agitation or retardation, constant fatigues, recurrent thoughts of death, moodiness, memory loss, and the like.

The cause of anxiety and depression are unknown; however, it is believed to involve a combination of genetic and environmental factors, with each playing a substantial role. The conditions may run in families and many genes are believed to be involved. Environmental factors may include psychological stress, trauma, and certain infections. Anxiety and depression are recognized as disorders by the US National Institutes of Health.

The treatment of anxiety and depression can be difficult. Recommendations often include psychotherapy, medication, or both. Psychotherapy, such as cognitive behavioral therapy (CBT) may also be helpful. The medications duloxetine, milnacipran or pregabalin may be used. Use of opioid pain medication is controversial, with some stating their usefulness is poorly supported by evidence and others saying that weak opioids may be reasonable if other medications are not effective. Dietary supplements lack evidence to support their use.

Anxiety and depression are estimated to affect 5-30% of the population. Women are affected about twice as often as men. Rates appear similar in different areas of the world and among different cultures, however it is estimated that, each year, roughly 5% of the world suffers from a depressive disorder and 12% of the population suffers from an anxiety disorder.

SUMMARY

There is a need for systems and methods for treating the symptoms of anxiety and depression. The present disclosure provides non-pharmaceutical methods and systems for treating symptoms of anxiety and depression.

For example, the present disclosure provides a method of treating anxiety or depression. The method includes administering a therapeutically effective amount of a sensory stimulus to the person, where the sensory stimulus includes one or more of a visual stimuli and an auditory stimuli.

The present disclosure also provides a method of treating anxiety or depression. The method includes administering a therapeutically effective amount of a sensory stimulus to a user. The sensory stimulus includes alternating between a first sensory stimuli and a second sensory stimuli. The a first sensory stimuli including simultaneously providing a first left visual stimuli pattern to a left eye of the user a first right auditory stimuli pattern to a right side of a head of the user. The second sensory stimuli including simultaneously providing a first right visual stimuli pattern to a right eye of the user and a first left auditory stimuli pattern to a left side of the head of the user. The first left auditory stimuli pattern or the first right auditory stimuli pattern includes a sequence of stimuli patterns including a first stimuli pattern, a second stimuli pattern, and a third stimuli pattern.

The present disclosure further provides a system for treating anxiety or depression. The system includes, in one implementation, a headset. The headset is configured to administer a therapeutically effective amount of a sensory stimulus to a user. The sensory stimulus includes a visual stimuli or an auditory stimuli.

It is another aspect to provide a method to treat one or more symptoms of anxiety and depression, where the symptoms may include one or more of anxiety, pain, depression, and lack of quality of sleep.

It is yet another aspect to provide a method of treating anxiety and depression. The method includes providing a headset to be worn by the person; and administering, with the headset, the therapeutically effective amount of a sensory stimulus to the person.

In certain implementations sensory stimulus is provided to a person using devices and methods described in U.S. patent application Ser. No. 15/360,808 (the '808 patent application) and in U.S. patent application Ser. No. in Ser. No. 15/910,252 (the '252 patent application). The '808 and '252 patent applications are co-owned with the present patent application and are both herein included by way of incorporation in their entirety.

BRIEF DESCRIPTION OF THE DRAWINGS

These features together with the various ancillary provisions and features which will become apparent to those skilled in the art from the following detailed description are attained by the method of the present disclosure, preferred implementations thereof being shown with reference to the accompanying drawings, by way of example only.

FIG. 5 is a table of one example of specification for a first treatment stimulus segment.

FIG. 6 is a table of one example of specification for a second treatment stimulus segment.

FIG. 7 is a table of one example of specification for a third treatment stimulus segment.

FIG. 8 is a chart of one example of results of a Pittsburgh Sleep Quality Index (PSQI) study.

Figure 1:
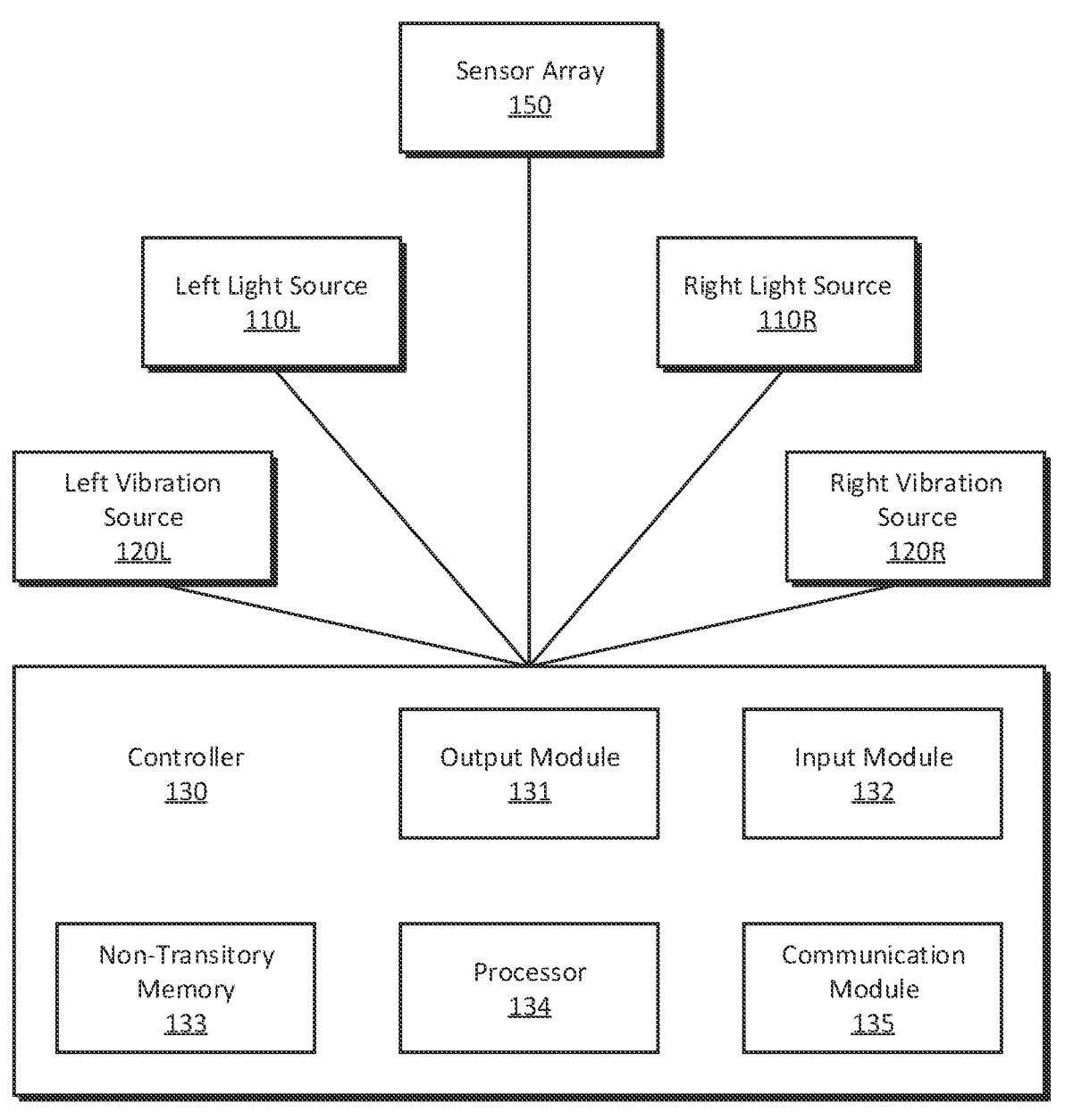
FIG. 1 is a block diagram of one example of a system that may be used to provide a therapeutic sensory stimulus to a person.

Reference symbols are used in the Figures to indicate certain components, aspects or features shown therein, with reference symbols common to more than one Figure indicating like components, aspects or features shown therein.

NOTATION AND NOMENCLATURE

Various terms are used to refer to particular system components. A particular component may be referred to commercially or otherwise by different names. Further, a particular component (or the same or similar component) may be referred to commercially or otherwise by different names. Consistent with this, nothing in the present disclosure shall be deemed to distinguish between components that differ only in name but not in function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections.

The terminology used herein is for the purpose of describing particular example implementations only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example implementations. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "left," "right," "inner," "outer," "beneath," "below," "lower," "above," "up," "upper," "top," "bottom," "down," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

"Real-time" may refer to less than or equal to 2 seconds. "Near real-time" may refer to any interaction of a sufficiently short time to enable two individuals to engage in a dialogue via such user interface, and will generally be less than 10 seconds (or any suitable proximate difference between two different times) but greater than 2 seconds.

DETAILED DESCRIPTION

Various implementations described herein are directed to non-pharmaceutical methods and systems of treating anxiety and depression. The methods include administering a therapeutically effective amount of a sensory stimulus to a person, resulting in a reduction of the person's anxiety and depression.

The sensory stimulus provided to the person as described herein is provided over a period of time and may, in certain implementations, comprise two or more simultaneous stimuli, such as a visual stimuli and an auditory stimuli. In addition, each sensory stimuli may include a temporal sequence of sensory stimuli patterns, such as a sequence of stimuli having different frequencies, and/or a stimuli that alternates between sensory organs, as by alternating between the eyes or ears or the person. In various implementations, the stimulus may include, but is not limited to, one or more of: a visual stimuli to one or both eyes of the person; an auditory stimuli to one or both ears of the person; and/or a tactile stimuli to the skin of the person.

FIG. 1 is a block diagram of one example of a system 100 that may be used to provide a therapeutic sensory stimulus to a person. The system 100 provides one or more stimuli outputs that a person using the system 100 may experience as an auditory stimuli, a visual stimuli, and/or tactile stimuli. The system 100 illustrated in FIG. 1 includes a left light source 110L, a right light source 110R, a left vibration source 120L, a right vibration source 120R, a controller 130, and a sensor assembly 150. The controller 130 independently controls and coordinates the actions of the light and vibration sources. Thus, for example, the system 100 may be positioned on the head of a user with the left light source 110L positioned over the left eye to provide a left visual stimulus, the right light source 110R positioned over the right eye to provide a right visual stimulus, the left vibration source 120L positioned to provide left ear auditory stimuli, and the right vibration source 120R positioned to provide right ear auditory stimuli.

In some implementations, the left light source 110L and the right light source 110R may each comprise light-emitting diodes, an incandescent light source having a wavelength filter, a fluorescent light source, a backlit LCD panel, or other light source configured to provide to the user light at a desired, predetermined wavelength or wavelength range.

In some implementations, the left vibration source 120L and the right vibration source 120R may each comprise earbuds, miniature speakers, or other vibration sources that can provide auditory stimuli to a user. Alternatively, or in addition, the left vibration source 120L and the right vibration source 120R may comprise bone conduction transducers in the audible frequency range to provide vibrations to the user's skull bone that is sensed as auditory by the user's ear. In some implementations, the left vibration source 120L and the right vibration source 120R may also produce vibrations that are sensed as tactile stimuli. Thus, for example, controller 130 may provide first signals to bone conduction transducers that vibrate or oscillate at a first frequency that can be interpreted by the user as auditory stimuli and may provide second signals at a second, lower frequency that can be interpreted as a tactile sensation by the user. In other words, bone conduction transducers may be adapted to provide both auditory and tactile stimulus to the user.

In some implementations, the left vibration source 120L and the right vibration source 120R provide output at specific one or more frequencies or a range of frequencies. In some implementations, the left vibration source 120L and the right vibration source 120R are separately controlled to provide output at certain times and to not provide output at other times. Thus, for example, a vibration source may be programmed to provide an output as an amplitude modulated audio frequency, which may be, for example and without limitation, 141 Hz, 174 Hz, 232 Hz or 256 Hz. Thus, in this example, the vibration source is the product of an audio frequency and a square wave.

Alternatively, or in addition, the left vibration source 120L and the right vibration source 120R provide signals of slightly different frequencies to the left and right ear. This results in a binaural beats effect, wherein the person perceives a sound at a frequency that is the difference between the frequency in the right ear and the frequency in the left ear. Thus, for example, when a person is provided with a 200 Hz audio frequency to the left ear and a 210 Hz audio frequency to the right ear, the person will perceive 200 Hz in the left ear, 210 Hz in the right ear, and 210 Hz–200 Hz=10 Hz which appear as being provided to both ears. This effect may be used to provide sound at brain wave frequencies separately from, or in combination with, the other methods described herein.

The sensor assembly 150 is configured to obtain one or more measurements from the user. Thus, for example and without limitation, the sensor assembly 150 may include, or is in communication with, a sensor that measures some property or characteristic of the user, including but not limited to, heart rate, heart rate variability, body temperature, or blood pressure, and includes electronics that provide a signal indicative of the measurement to the controller 130. In some implementations, the sensors are connected to sensor assembly 150 by wired or wireless connectors. Thus, in various implementations, the sensors may include one or more: electrodes for sensing electrical activity in the brain, as in a two or four lead electrocephalogram (EEG), a temperature sensor, and/or a heartbeat sensor, or one or more electromyography (EMG) sensors positioned, for example and without limitation, to measure eye movement to ascertain when REM sleep is reached, and/or to measure muscle tone to aid in determining states of relaxation. In some implementations, the controller 130 utilizes the signal from the sensor assembly 150 to modify the intensity and/or timing of the light and vibration sources.

The controller 130 illustrated in FIG. 1 includes an output module 131, an input module 132, a non-transitory memory 133, a processor 134, and a communication module 135. The output module 131 is configured to provide signals to actuate the left light source 110L, the right light source 110R, the left vibration source 120L, the right vibration source 120R, and any other components that provide sensory input to the user. The input module 132 is configured to accept signals from the sensor assembly 150. The non-transitory memory 133 stores programming and data for the system 100. The non-transitory memory 133 includes instructions that are accessible to the processor 134 for operating the components that provide sensory input to the user, including but not limited to the left light source 110L, the right light source 110R, the left vibration source 120L, and the right vibration source 120R. The sensory input may include accepting input provided to the input module 132 and modifying signals provided to components that provide sensory input to the user, including but not limited to the left light source 110L, the right light source 110R, the left vibration source 120L, and the right vibration source 120R. The communications module 135 provides for the transfer of information to or from the controller 130 by wired or wireless means.

In an alternative implementation, the system 100 may also provide tactile stimulus to a user by including a left tactile stimulus source and a right tactile stimulus source (not shown), each of which may be individually controlled and coordinated with the controller 130 to provide tactile stimuli to a user of the system 100.

Figures 2A, 2B, 2C:
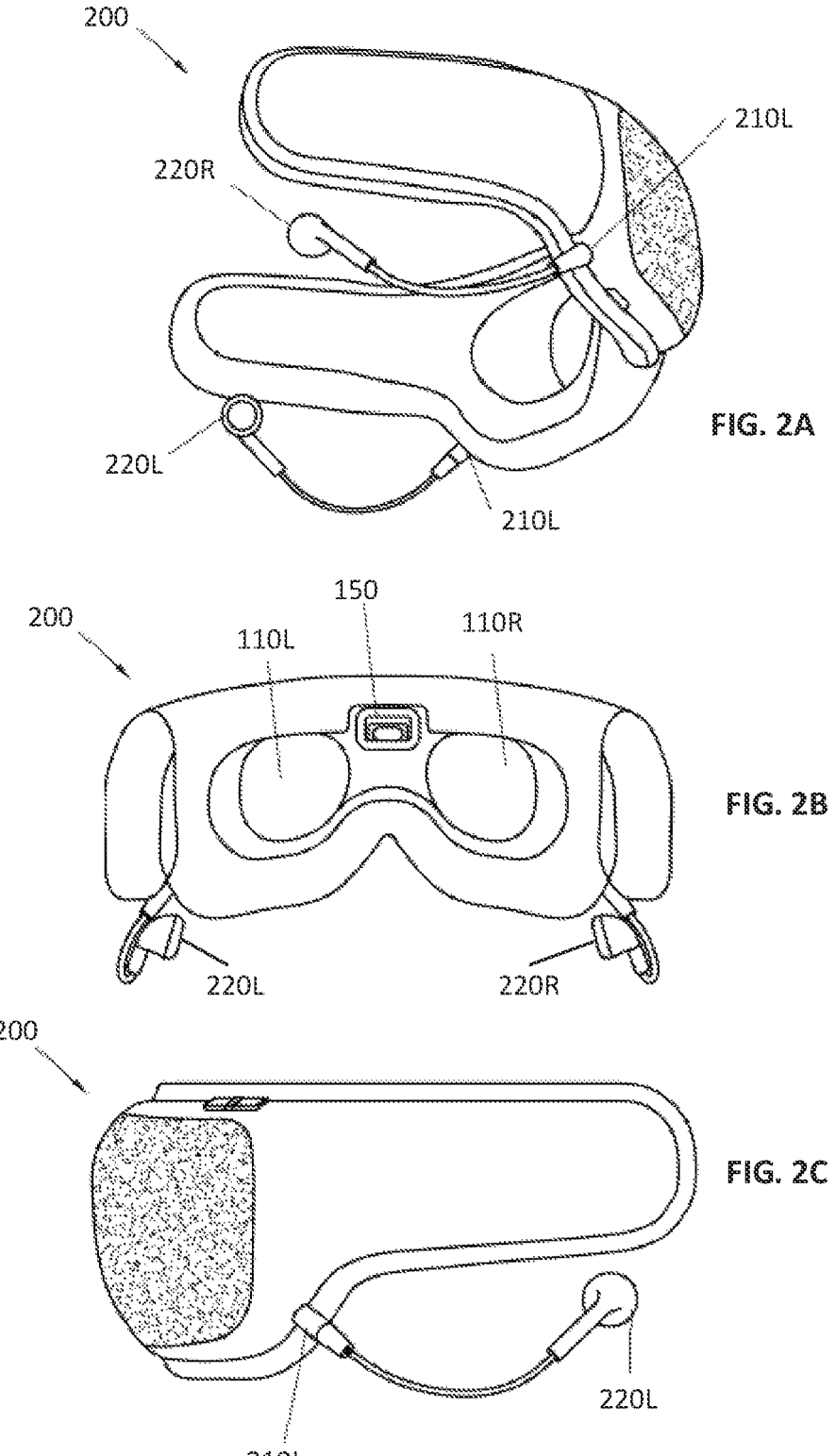
FIG. 2A is a bottom right perspective view of one example of a headset that may be used to provide a therapeutic sensory stimulus to a person.
FIG. 2B is a rear view of the headset illustrated in FIG. 2A.
FIG. 2C is a left side view of the headset illustrated in FIG. 2A.
Figure 3:
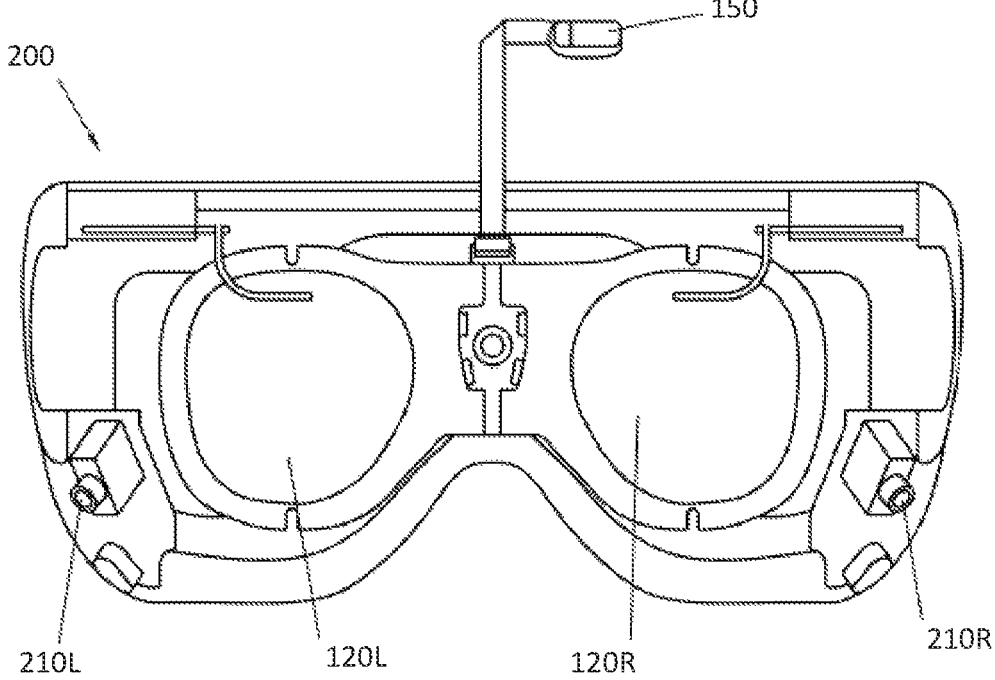
FIG. 3 is an exploded front view of the headset illustrated in FIG. 2A.

FIG. 2A is a bottom right perspective view of an example of a headset 200. FIG. 2B is a rear view of the headset 200. FIG. 2C is a left side view of the headset 200. FIG. 3 is an exploded front view of the headset 200. The headset 200 is generally similar to the system 100 except as explicitly noted.

The headset 200 illustrated in FIGS. 2A-2C and 3 includes the sensor assembly 150, the controller 130, the left light source 110L, the right light source 110R, a left audio jack 210L, a right audio jack 210R, a left earbud 220L, and a right earbud 220R. The sensor assembly 150 includes a biometric sensor system, such as that which is sold under the name of VALENCELL BENCHMARK™ (Raleigh, NC), that includes an infrared light source and detector, which can be used to detect heart rate using pulse oximetry, an accelerator, and a processing unit. The sensor assembly 150 includes a sensor module circuit board that contains a digital optical detector system. This detector controls the LEDs and converts the optical signals reflected from the user's skin to digital format and communicates over the internal I2C bus to the PerformTek® processor. The accelerometer is also read via the internal I2C bus for activity signal.

In one implementation, controller 130 includes a Nordic Semiconductor ASA (Oslo, Norway) model NRF51822 Multiprotocol BLUETOOTH® low energy/2.4 GHz RF System on Chip, and a VLSI Solution (Tampere, Finland) model VS1000 audio module.

In one implementation, the left light source 110L and the right light source 110R are Lite-On, Inc. (Milpitas, CA) Bin G3/W2/AU model LTST-020VSKT LEDS. In some implementations, the left earbud 220L (one example of a "left vibration source") and the right earbud 220R (one example of a "right vibration source") are Basen Technology Co, Ltd model PN: OEM-E170a earbuds.

In one implementation, the sensor assembly 150 also includes a PerformTek® processor which polls sensor data over the internal I2C bus and converts the raw measurements into data registers of biometric values (i.e. Heart Rate, Cadence, VO2) and processes those values further into higher level user assessments (i.e. Calories Burned, Distance, VO2 max, fitness level, and the period between heart rate beats (the Heart Rate Interval, or RR Interval)). The PerformTek® processor runs algorithms to convert the raw signals to a register array of biometric values and high-level assessments. These values are available for reading via the UART or I2C firmware interface. In addition, sensor module diagnostics such as signal quality, error codes, and serial number ID are available.

The sensor assembly 150 further includes control lines for interfacing controller 130 with the PerformTek® processor include a Power On Self-Test (POST), UART or I2C communication interface, and a wake-from-standby line (WAKE). The host processor can control much of the functionality of the sensor module via a software protocol interface over the UART or I2C interface.

In one implementation, the sensor assembly 150 determines a current heart rate, and/or an inter-beat R-R interval which is provided to the controller 130. In another implementation, the sensor assembly 150 also provides accelerometer data to the controller 130.

In yet another implementation, the sensor assembly 150 includes one or more EEG sensors, as are known in the field, and provides brain electrical activity measurements to the controller 130.

In another implementation, the sensor assembly 150 includes one or more EMG sensors positioned, for example and without limitation, to measure eye movement to ascertain when rapid eye movement (REM) sleep is reached, and/or to measure muscle tone to aid in determining states of relaxation. EMG sensors, as are known in the field, and provides brain electrical activity the measurements to the controller 130.

The left earbud 220L may be plugged into the left audio jack 210L and the right earbud 220R may be plugged into the right audio jack 210R. Alternatively, stereo headphones (not shown) may be plugged into one of the left audio jack 210L or the right audio jack 210R, where the jacks are appropriately programmed to provide stereo sound to the headphones.

Figure 4:
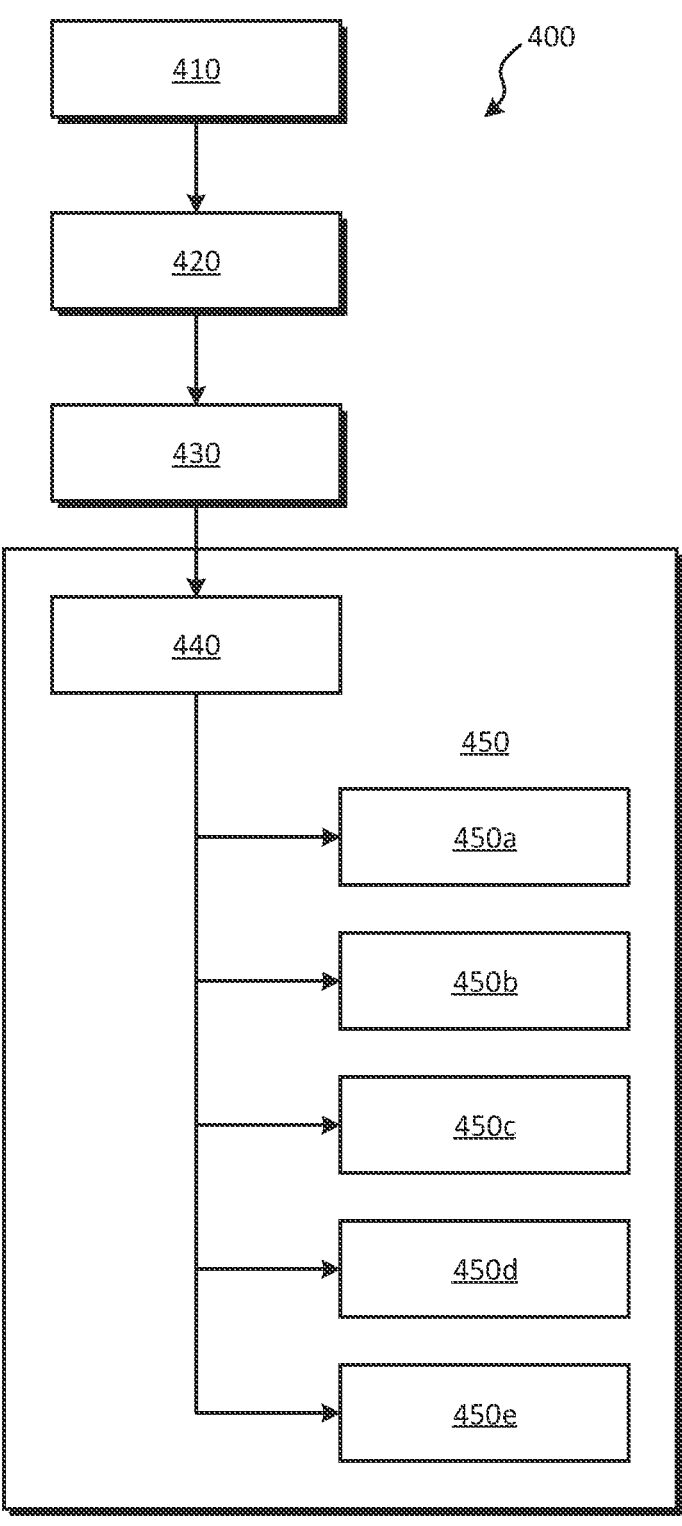
FIG. 4 is a flow diagram of an example of a method for providing therapeutic auditory, visual, and/or tactile stimulus.

FIG. 4 shows a flow chart of an example of a method 400 for providing therapeutic auditory, visual, and/or tactile stimulus using, for example and without limitation, one of the system 100 or the headset 200. At block 410, a subject having anxiety and/or depression, or who wishes to undergo a treatment for managing the anxiety and/or depression, is identified. At block 420, the subject is provided the therapeutic system or headwear, such as headset 200 as described above. At block 430, the subject places the headset 200 on their head. At block 440, the headset 200 executes programming 450 provided in the controller 130 to provide stimuli to the subject. The programming 450 provides two or more of auditory, visual, and/or tactile stimulus to the subject, and thus, for example, may provide power to activate the left light source 110L, the right light source 110R, the left vibration source 120L, the right vibration source 120R, or a combination thereof. The programming also includes modifying the auditory, visual, and/or stimuli in response to measurements obtained by the sensor assembly 150 and provided to the controller 130.

As discussed above and herein, the left vibration source 120L and the right vibration source 120R may each comprise bone conduction transducer that may provide both auditory and tactile stimulus.

In certain implementations, providing two or more of auditory, visual, and/or tactile stimulus concurrently may provide improved therapeutic benefits as compared to providing only one of auditory, visual, or tactile stimulus at one time. The two or more auditory, visual, and/or tactile stimulus may thus combine to provide the improved therapeutic benefits, for example (i.e., the two or more auditory, visual, and/or tactile stimulus may synergize in a way to provide improved results over providing two of the stimuli individually).

Exemplary instructions for providing stimuli may be provided, for example, by programming 450, which includes one or more subroutines. One such subroutine is subroutine 450e, which analyzes measurements obtained from the sensor assembly 150 and stores the analyzed measurements in the non-transitory memory 113. Subroutine 450a includes instructions for the simultaneous activation of all active auditory, visual, and/or tactile stimulus sources. Optionally, the activation of all sources may include the activation of tactile stimulation to run throughout all subsequent auditory and/or visual stimulation. Another exemplary subroutine 450b may include instructions for alternating the left auditory, visual, and/or tactile stimulus sources with the right auditory, visual, and/or tactile stimulus sources (i.e., the left stimuli and right stimuli take turns being active). Another exemplary subroutine 450c may include instructions for alternating the visual sources with the auditory and/or tactile sources (i.e., the visual stimuli and the auditory/tactile stimuli take turns being active). Another exemplary subroutine 450d may include instructions for alternating the left auditory and/or tactile source and the right visual source with the right auditory and/or tactile source and the left visual source (i.e., opposite auditory/tactile stimuli take turns being active).

In some implementations, one or more of subroutines 450a, 450b, 450c, or 450d, access the analyzed measurements from subroutine 450e and modifies the instructions they provide to the auditory, visual, and/or tactile stimuli depending on real-time or near real-time measurements of the user obtained from the sensor assembly 150. Such programming is further described below.

At block 440, programming 450, including by not limited to subroutines 450a, 450b, 450c, and 450d, may each be applied one or more times, individually or in combination with one another. The programming may, in addition, provide sequences of output in subroutines 450a, 450b, 450c, and 450d at different frequencies and/or timings. Thus, for example the subroutines may provide output at specific frequencies that change as the subroutine is repeated.

In certain implementations, the pulses that determine the amplitude modulation above are essentially square waves and thus, as determined by a Fourier analysis, are formed of sinusoidal components at the pulse frequency and at higher harmonics. As an approximation, an ideal square wave with a pulse frequency of P contains only odd-integer harmonic frequencies at $(2k-1)*P$, where $k=1, 2, 3 \ldots$, which contain a fraction $(2/\pi)/(2k-1)$ of the total power in the square wave. Thus, for example, the signal power in a square wave with a pulse frequency of 4 Hz includes a 63% of the power at 4 Hz, 21% of the power at 12 Hz, 13% of the power at 20, etc., If the square wave does not have equal on and off periods, then the pulse frequency will also contain even-integer harmonic frequencies.

Thus, for example, subroutine 450a may provide amplitude modulated auditory output to the left vibration source 120L or the right vibration source 120R at a carrier audio frequency of 256 Hz that is turned on and off, that is it is pulsed, at a pulse frequency of 1 Hz for 2 minutes, or may provide amplitude modulated light output to the left light source 110L or the right light source 110R that produces at a carrier light wavelength 580 nm that is turned on and off, that is it is pulsed at a at a pulse frequency of 1 Hz for 2 minutes. This square pulse auditory or light signal thus generates signals at a frequency of 1 Hz in addition to higher harmonics.

In certain implementations, the subroutines described herein generate pulses having sinusoidal components that correspond with certain known brain wave frequencies, which are generally accepted as being delta waves (0.1 to 4.0 Hz), theta brain waves (4 to 7 Hz), alpha brain waves (8 to 15 Hz), beta waves (16 to 31 Hz), and gamma brain waves (32 to 100 Hz). Thus, certain implementations include pulse frequencies of from 3.75 Hz to 4.25 Hz (theta brain waves), of from 1.25 Hz to 1.75 Hz (delta waves), and/or from 0.25 Hz and 0.75 Hz (delta waves).

In addition, by alternating the output between left and right channels, the brain may be stimulated in a way that it is forced to communicate between the left and right sides of the brain. This forced communication, for example, can allow PTSD memories to be wired to both sides of the brain, thereby stopping undesirable flashbacks. It can also create an enhanced relaxation effect, allowing for deeper relaxation and anxiety and/or depression management.

In one implementation, the system 100 provides a stimulus that includes visual and auditory stimuli over three temporally sequential segments—a first segment where stimuli occurs at a first frequency, followed by a second segment where stimuli occurs at a second frequency, which was followed by a third segment where stimuli occurs at a third frequency. Each time segment included sub-segments of visual and auditory stimuli, where each sub-segment was determined by one of the subroutines described above, for example. The visual stimuli were provided by pulsing light at a wavelength of 580 nm at certain pulse frequencies and by pulsing auditory signals at a frequency of 256 Hz at certain pulse frequencies.

In one implementation, a treatment stimulus lasted for 16 minutes, and may be understood by reference to Table 500 in FIG. 5, Table 600 in FIG. 6, and Table 700 in FIG. 7. Table 500 contains specifications for the first segment ("Segment A"). Table 600 contains specifications for the next, second time segment ("Segment B"). Table 700 contains specifications for the last time segment ("Segment C"). Each of the Segments stimuli patterns at a different pulse frequency. Specifically, Segment A cycles the stimuli through a block of four Segment A stimuli patterns for a total of 2 minutes, Segment B cycles the stimuli through a block of four Segment B stimuli patterns for a total of 2 minutes, and Segment C cycles the stimuli through a block of six Segment C stimuli patterns for a total of 12 minutes.

More specifically, in the four Segment A stimuli patterns, as shown in Table 500 as Blocks A1, A2, A3, and A4 respectively, the auditory and light outputs cycle 115 or 116 times between being on for 0.1277 seconds and then being off for 0.1277 seconds (that is, at a pulse frequency of 3.9 Hz), followed by no output for 0.5 seconds. In the Segment B stimuli patterns, as shown in Table 600 as Blocks B1, B2, B3 and B4, the auditory and light outputs cycle 44 or 45 times between being on for 0.3333 seconds and then being off for 0.3333 seconds (that is, at a pulse frequency of 1.5 Hz) followed by no output for 0.5 seconds. In the Segment C stimuli patterns, as shown in Table 700 and labeled Blocks C1, C2, C3 and C4, the auditory and light outputs cycle 14 or 15 times between being on for 1 second and then being off for 1 second (that is, a pulse frequency of 0.5 Hz), followed by no output for 1 second. Blocks A1, B1, and C1 pulse the right and left sides of both the light and auditory together, with all outputs are synchronized to be on or off at the same time, as provided by subroutine 450a. Blocks A2, B2, and C2 synchronize the left side light and auditory output, and the right side light and auditory output to be opposite to one another, as provided by subroutine 450b. Blocks A3, B3, and C3 synchronize both lights together to be opposite to both auditory outputs, as provided by subroutine 450c. Blocks A4, B4, and C4 synchronize the right auditory and light to be opposite to the left auditory and light outputs, as provided by subroutine 450d.

At block 440, subroutine 450e receives measurements from the sensor assembly 150 and stores analyzed measurements. In one implementation, the sensor assembly 150 provides instantaneous, or nearly instantaneous, measurements from the user. Thus, for example and without limitation, the sensor assembly 150 provides a sequence of measurements of beat-to-beat intervals of the heart of the user, that is, the time interval between the last two heart beats, which is also referred to, without limitation, as the RR intervals. The controller 130 then computes and stores values of the heart rate variability (HRV), which is a mathematical representation of the physiological phenomenon of variation in the time interval between heartbeats.

In certain implementations, a time-domain calculation of RR intervals, as obtained by the sensor assembly 150, is used to compute the HRV. Thus, for example, the sequence of RR intervals ("$RR_i$") is accepted from the sensor assembly 150 and stored in the non-transitory memory 133. After the accumulation $RR_i$ for a period of time, T, the HRV is calculated as approximated by the root mean square of successive differences between adjacent RRs, or RMSSD. Thus, at a time T from the beginning of the accumulation of data, if N consecutive RR intervals are stored in the non-transitory memory 133, the following calculation is performed by the processor 134 according to a program stored in the memory:

$$RMSSD = \sqrt{\frac{1}{N-1}\left(\sum_{i=1}^{N-1}(RR_{i+1} - RR_i)^2\right)}$$

The initial value of RMSSD (that is, $RMSSD_0$) is stored in the non-transitory memory 133 as a baseline. Thereafter, at the end of each period T, the calculation of RMSSD is repeated covering that time period. As a result, a sequence of $RMSSD_j$ values are computed. Next the difference between the current RMSSD value and the baseline $RMSSD_0$ is computed as $\Delta RMSSD_j = RMSSD_j - RMSSD_0$. $\Delta RMSSD$ is a measure of the change between the current HRV and the baseline, initial HRV.

In general, it is realized by those skilled in the art, that an increased in HRV is associated with a relaxed state, or a sleep state, and that a decrease in HRV is associated with a less relaxed, or stressed, state. For uses of the system 100 intended to calm a person or to induce sleep, a positive $\Delta RMSSD$ indicates that the person is becoming relaxed and that the system is working as intended. A negative $\Delta RMSSD$ indicates that the person is not becoming more relaxed. In one implementation, an indication that the person is relaxed ($\Delta RMSSD > 0$) is used to modify the treatment by reducing the treatment time and/or intensity of the stimuli, and an indication that the person is less relaxed ($\Delta RMSSD < 0$) is 11                                                          12 used to modify the treatment to increase the treatment time and/or the intensity of the stimuli.

In certain implementations, Kubios HRV software (manufactured by Kuopio, Finland) is used to analyze the RR intervals to provide additional HRV related data. Thus, for example, one useful measure for analyzing HRV is the fraction of the power of the HRV signal that occurs in certain frequency ranges. Thus, for example, one measure which is referred to herein as HRV-HFnu is obtained by taking the Fourier transform of the HRV signal and computing the ratio of the power of the HRV signal from 0.15 to 0.40 Hz ("high frequencies") to the total power of the HRV signal.

The calculations described above are provided by way of explanation and are not meant to limit the scope of the calculations or how the operation of the system 100 is or is not modified using HRV measurements.

Although the above steps show method 400 of treating a patient in accordance with implementations, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 400 may be performed with the circuitry as described herein, for example, circuitry of the controller 130 such as one or more of a processor or logic circuitry such as a central processing unit (CPU) or a programmable array logic for field programmable gate array. The circuitry may be programmed to provide one or more of the steps of the method 400, and the program may comprise program instructions stored on a computer readable memory or programmed steps of the logic circuitry such as the programmable array logic or the field programmable gate array, for example.

A Study of the Treatment of Anxiety and Depression

A study was conducted on the effectiveness of the inventive method for treating pain, such as being associated with anxiety and depression using the headset 200. A single arm trial was conducted by PI Dr. Mark Kuchar, DC, CSCS at Southpointe Clinic, Colorado Protocol A group of eight participants were selected for testing the effectiveness of the headset 200 in treating pain associated with anxiety and depression. Each of the participants were considered to be treatment resistant—that is, they experienced no improvement from other modalities or placebo and had previously failed on all drug regimens and a ninety day best standard of care protocol.

The study was divided into three phases: Screening and Baseline, Treatment, and Follow-up. Each patient participated in the study for up to thirty days, including Screening and Baseline (up to seven days), Treatment (fifteen days), and Follow-up (up to ten days).

Screening and Baseline procedures were performed within seven days of admission to the Treatment Phase. Participants were instructed to rate their pain intensity and sleep quality, and record their concomitant medication use on a daily basis using a logbook.

On Day one of the Treatment Phase, eligible participants were instructed on the use of receiving a treatment from the headset 200 and used the device for the first time under clinic supervision; all other uses of the device were conducted at home. During the Treatment Phase, participants underwent at least two daily treatments with headset 200, including a treatment immediately prior to bedtime. Additional treatments were allowed, as needed, at the participant's discretion.

Pain intensity was assessed, as described subsequently, prior to each treatment and, with the exception of the bedtime treatment, within five minutes of completion of each treatment. Participants recorded pain intensity and sleep quality, as discussed subsequently, upon waking in the morning, and recorded the use of medications/non-pharmacological therapies on a daily basis prior to bedtime.

During the Treatment Phase, participants attended the study site on Day one of the Treatment Phase, and on Day fifteen of the Treatment Phase. At each study visit, assessments of sleep quality, depression and anxiety, use of concomitant medications/non-pharmacological therapies and compliance with the headset 200 were completed. On Day eight of the Treatment Phase (+/− one day) participants received a phone call to confirm compliance with use of the headset 200, answer questions and check for adverse events (AEs). Assessments of AEs and treatment acceptability were also be conducted during the Treatment Phase. A Follow-up call was scheduled within seven days (±three days) of completing the Treatment Phase.

The following concomitant medications and therapies were permitted during the study:

Nonsteroidal anti-inflammatory drugs (NTHEs) were permitted occasionally for headache, fever, or other indications aside from chronic pain, for no more than three consecutive days and no more than the maximum daily recommended dose. NTHEs were not be permitted during the Baseline period and the last three days of the Treatment Phase.

Opioid and non-opioid analgesics were permitted, but participants were required to be on a stable dose (±20% dose and timing of administration) for at least fourteen days prior to enrollment.

Anti-constipation medications.

Aspirin at doses less or equal to 325 mg/day for cardiovascular prophylaxis.

The following medications and therapies were permitted, and remained stable (±20% dose and timing of administration) throughout the duration of the participant's participation in the study: muscle relaxants, hypnotics (eszopiclone, zolpidem, zaleplon), antidepressants, anticonvulsants, benzodiazepines, physical therapy, biofeedback therapy, acupuncture therapy, and herbal remedies (except for St. John's Wort).

On a case-by-case basis, the investigator was permitted to allow the use of some concomitant medications, for example, to treat an AE, as long as the investigator determined that the medication would not affect the patient's safety or study integrity. The following regimens were permitted:

Supplemental medications including either 1000 mg acetaminophen up to two times per day, 550 mg naproxen up to two times per day, or 800 mg/day ibuprofen up to four times per day, up to the maximum daily dose (i.e., either up to 2000 mg/day acetaminophen, up to 1100 mg/day naproxen, or up to 3200 mg/day ibuprofen).

Use of any analgesic medications or non-pharmacological therapies where be recorded (date, time, medication name, dose, regimen, etc.).

All eight participants elected to continue using the device and stated an intention to use it as part of their treatment regimen, and one participant was able to discontinue use of alprazolam (Xanax) early in study.

Measures of Symptoms of Anxiety and Depression

In the study discussed subsequently, test subjects were provided with a number of sensory stimuli and their response to the treatment was determined using subjective measures using the following questionnaires:

Pain Intensity Visual Analog Scale (VAS) (or "VAS-Pain"), which prompts the patient to rate "How I feel" on a VAS, ranging from between "No Pain," which is assigned a value of zero, to "Worst Pain Imaginable," which is assigned a value of 100.

Pittsburgh Sleep Quality Index (PSQI), which presents questions used to measure the quality and patterns of sleep in adults). It differentiates "poor" from "good" sleep quality by measuring seven areas (components): subjective sleep quality, sleep latency, sleep duration, habitual sleep efficiency, sleep disturbances, use of sleeping medications, and daytime dysfunction over the last month. The score on the PSQI ranges from 0-21, where higher scores indicate worse sleep quality.

Patient Health Questionnaire (PHQ-9), which presents questions related to depression. The PHQ-9 is a validated tool for screening, diagnosing, monitoring and measuring depression severity, and scores each of the 9 Diagnostic and Statistical Manual of Mental Disorder, Fourth Edition (DSM-IV) related criteria.

Generalized Anxiety Disorder 7-item (GAD-7) Scale, presents question to the patient for screening and measuring severity of generalized anxiety. See, for example https://www.mdcalc.com/gad-7-general-anxiety-disorder-7. The score on the GAD-7 Scale range from 0-21, where a score of 5-9 is interpreted as a level of mild anxiety, a score of 10-14 is interpreted as a moderate level of anxiety, having possible clinical significance, and a score of 15 or greater is interpreted as a severe level of anxiety, likely warranting active treatment.

Patient Global Impression of Change (PGIC) is a commonly used tool that is recommended to assess a patient's overall satisfaction with their treatment. The patent is prompted to indicate whether there has been any change in their activity limitations, symptoms, emotions and overall quality of life, as related to their pain condition, since the start of the study (1=No change to 7=A great deal better). In addition, patients rate the degree of change since beginning treatment on a 0 (Much Better) to 10 (Much Worse) scale. Patients completed the PGIC on Day 15 or early discontinuation.

Likelihood to Use Device Again question, in which patients answered the question "If the device was available, how likely would you be to continue use of the device," of headset 200. Response options range from extremely likely, very likely, somewhat likely, not very likely, to not at all likely.

Study Results

The following is a comparison of the average baseline measures if pain, anxiety, depression, quality of sleep for all 8 participants with the same measures after the Treatment Phase.

The average VAS-Pain score for all study participants was 62.7 at baseline and 46.5 at the end of treatment, with a P value of 0.0754. This is a 26% decrease in the VAS-Pain score, corresponding to a decrease in perceived pain from "intense" to "distressing." Further, it was found that the treatment worked best for participants with the greatest amount of pain, as those with the severest amounts of pain patients had a reduction of VAS-Pain scores of 49%.

The average GAD 7 scale scores, which is a measure of anxiety, was 11 at baseline and 6.25 at the end of treatment, with a P value of 0.0096, which indicates a high level of level of statistical certainty. This is a 43% decrease in the anxiety scores and corresponds to a decrease in perceived anxiety from "moderate" to "mild."

The average PHQ9 scale scores, which is a measure of depression was 15.5 before the study and 8.75 at the end of treatment, with a P value of 0.0024, which indicates a high level of level of statistical certainty. This is a 44% decrease in the anxiety scores and corresponds to a decrease in perceived depression from "moderately severe" to "mild."

Figure 8:
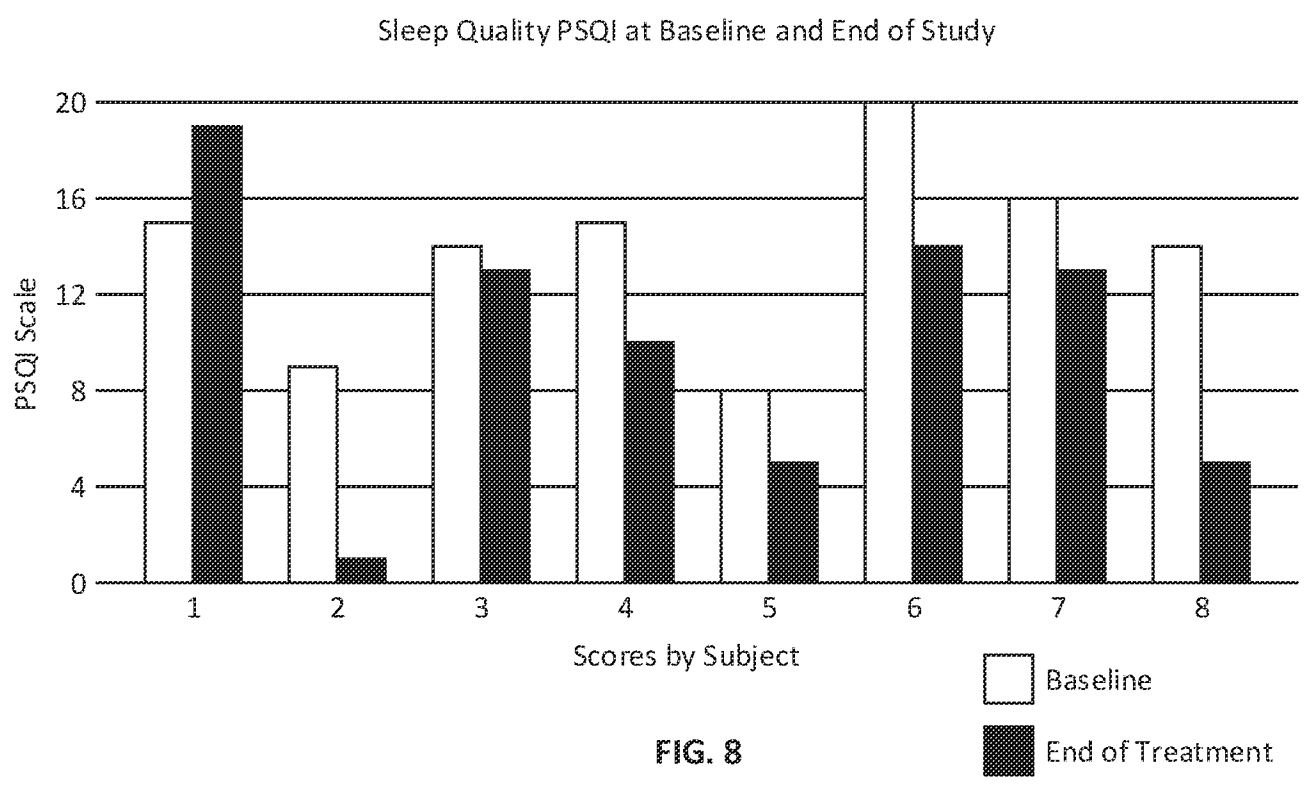

The PSQI scale scores for each participant is illustrated in the chart included in FIG. 8. The results indicate that the quality of sleep improved by 28% over the course of treatment, with a P value of 0.0033, which indicates a high level of level of statistical certainty.

The results of the Likelihood to Use Device Again survey at the end of the Treatment Phase indicated that six of eight participants of the headset 200 would be "Very Likely" to use the device, if it was offered to them.

The results of the Quality of Life Likelihood to Adopt Device survey at the end of the Treatment Phase indicated that six of eight participants of the headset 200 would be "Very Likely" to use the device, if it was offered to them.

The results of the Patient Global Impression of Change (PGIC) survey shows that most patients indicated that the Treatment Phase provided a "Definite improvement that has made a real and worthwhile difference" or higher on the PGIC survey and provided an improvement in the quality of life.

One implementation of each of the methods described herein is in the form of a computer program that executes on a processing system, e.g., a one or more processors that are part of the system 100. Thus, as will be appreciated by those skilled in the art, implementations of the present disclosure may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, aspects of the present disclosure may take the form of a method, an entirely hardware implementation, an entirely software implementation or an implementation combining software and hardware aspects. Furthermore, the present disclosure may take the form of carrier medium (e.g., a computer program product on a computer-readable storage medium) carrying computer-readable program code segments embodied in the medium. Any suitable computer readable medium may be used including a magnetic storage device such as a diskette or a hard disk, or an optical storage device such as a CD-ROM.

Reference throughout this specification to "one implementation" or "an implementation" means that a particular feature, structure, or characteristic described in connection with the implementation is included in at least one implementation of the present disclosure. Thus, appearances of the phrases "in one implementation" or "in an implementation" in various places throughout this specification are not necessarily all referring to the same implementation. Furthermore, the particular features, structures, or characteristics may be combined in any suitable manner, as would be apparent to one of ordinary skill in the art from this disclosure, in one or more implementations.

Similarly, it should be appreciated that in the above description of exemplary implementations of the present disclosure, various features of the present disclosure are sometimes grouped together in a single implementation, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed implementation. Thus, the claims following the Detailed Description are hereby expressly incorporated into this Detailed Description, with each claim standing on its own as a separate implementation of the present disclosure.

Consistent with the above disclosure, the examples of systems and methods enumerated in the following clauses are specifically contemplated and are intended as a non-limiting set of examples.

What is claimed is:

1. A method of treating anxiety or depression, comprising:
administering a therapeutically effective amount of a bilaterally alternating sensory stimulus to a user via a headset, wherein the sensory stimulus includes a visual stimuli or an auditory stimuli;
obtaining a sequence of measurements of beat-to-beat intervals of a heart of the user using a heart rate sensor;
calculating values of heart rate variability using the sequence of measurements of beat-to-beat intervals of the heart of the user, including first and second values of heart rate variability respectively corresponding to a first time period and a second time period that is later than the first time period;
calculating a change in heart rate variability based on at least the first and second values of heart rate variability;
determining a state of the user based on the calculated change in heart rate variability, including determining a first state of the user based on the calculated change being positive and determining a second state of the user based on the calculated change being negative; and
modifying the sensory stimulus according to the state of the user, including reducing an intensity of the sensory stimulus based on the user being in the first state and increasing an intensity of the sensory stimulus based on the user being in the second state,
wherein the sensory stimulus further includes a first stimuli pattern and a second stimuli pattern that is different than the first stimuli pattern,
wherein the first stimuli pattern includes a first repetitive component corresponding to at least one of a delta, theta, or alpha brain wave frequency, and wherein the second stimuli pattern includes a second repetitive component corresponding to a different duration of applied stimuli at the at least one delta, theta, or alpha brain wave frequency.

2. The method of claim 1, wherein the visual stimuli includes a sinusoidally varying light generated by a light source.

3. The method of claim 1, wherein the auditory stimuli includes an amplitude modulated audio frequency.

4. The method of claim 1, wherein the first stimuli pattern has a first pulse frequency, and wherein the second stimuli pattern has a second pulse frequency that is different than the first pulse frequency.

5. The method of claim 4, wherein the first stimuli pattern includes a first sinusoidal component that is between 3.75 Hertz (Hz) and 4.25 Hz, is between 1.25 Hz and 1.75 Hz, or is between 0.25 Hz and 0.75 Hz, and wherein the second stimuli pattern includes a second sinusoidal component that is between 3.75 Hz and 4.25 Hz, is between 1.25 Hz and 1.75 Hz, or is between 0.25 Hz and 0.75 Hz.

6. The method of claim 4, wherein the sensory stimulus further includes a third stimuli pattern that is different than the first stimuli pattern and the second stimuli pattern.

7. The method of claim 6, wherein the first stimuli pattern includes a first sinusoidal component that is between 3.75 Hertz (Hz) and 4.25 Hz, is between 1.25 Hz and 1.75 Hz, or is between 0.25 Hz and 0.75 Hz, wherein the second stimuli pattern includes a second sinusoidal component that is between 3.75 Hz and 4.25 Hz, is between 1.25 Hz and 1.75 Hz, or is between 0.25 Hz and 0.75 Hz, and wherein the third stimuli pattern includes a third sinusoidal component that is between 3.75 Hz and 4.25 Hz, is between 1.25 Hz and 1.75 Hz, or is between 0.25 Hz and 0.75 Hz.

8. The method of claim 1, wherein the sensory stimulus further includes a third stimuli pattern, and wherein the third stimuli pattern includes a third repetitive component corresponding to a second different duration of applied stimuli at the at least one delta, theta, or alpha brain wave frequency.

9. The method of claim 1, further comprising:
obtaining a measurement of the user using at least one additional sensor;
determining the state of the user from the measurement of the user using the at least one additional sensor; and
modifying the sensory stimulus according to the state of the user.

10. The method of claim 9, wherein the at least one additional sensor includes at least one selected from the group consisting of a temperature sensor, a motion sensor, a galvanic skin response sensor, an accelerometer, an electroencephalogram sensor, or an electromyography sensor.

11. The method of claim 9, wherein the state of the user includes at least one state selected from the group consisting of a state of sleep, a change in a level of relaxation, and a change in a level of arousal.

12. The method of claim 9, further comprising:
providing the headset to be worn by the user, wherein administering the therapeutically effective amount of the sensory stimulus to the user is performed subsequent to providing the headset.

\* \* \* \* \*